(12) United States Patent
Melanson

(10) Patent No.: US 11,642,571 B2
(45) Date of Patent: May 9, 2023

(54) METHOD AND SYSTEM FOR UTILIZING RADIO-OPAQUE FILLERS IN MULTIPLE LAYERS OF GOLF BALLS

(71) Applicant: Callaway Golf Company, Carlsbad, CA (US)

(72) Inventor: David M. Melanson, Chicopee, MA (US)

(73) Assignee: Topgolf Callaway Brands Corp., Carlsbad, CA (US)

( * ) Notice: Subject to any disclaimer, the term of this patent is extended or adjusted under 35 U.S.C. 154(b) by 0 days.

(21) Appl. No.: 17/495,074

(22) Filed: Oct. 6, 2021

(65) Prior Publication Data

US 2022/0023721 A1   Jan. 27, 2022

Related U.S. Application Data

(63) Continuation-in-part of application No. 17/322,584, filed on May 17, 2021, now Pat. No. 11,185,741.

(60) Provisional application No. 63/030,494, filed on May 27, 2020.

(51) Int. Cl.
  *A63B 37/06*  (2006.01)
  *A63B 37/00*  (2006.01)
  *G01N 23/04*  (2018.01)

(52) U.S. Cl.
  CPC ...... *A63B 37/0024* (2013.01); *A63B 37/0035* (2013.01); *A63B 37/0039* (2013.01); *A63B 37/0051* (2013.01); *A63B 37/0066* (2013.01); *A63B 37/0075* (2013.01); *A63B 37/0076* (2013.01); *A63B 37/0078* (2013.01); *G01N 23/04* (2013.01)

(58) Field of Classification Search
  CPC .. A63B 37/005; A63B 37/0066; A63B 37/007
  USPC ......................................................... 473/373
  See application file for complete search history.

(56) References Cited

U.S. PATENT DOCUMENTS

| | | | | |
|---|---|---|---|---|
| 5,810,678 A * | 9/1998 | Cavallaro | ................. | C08L 9/00 473/378 |
| 5,879,244 A * | 3/1999 | Hwang | ..................... | C08K 3/08 473/378 |
| 2006/0172823 A1* | 8/2006 | Loper | ................. | A63B 37/0003 473/378 |
| 2012/0184396 A1* | 7/2012 | Sullivan | ............. | A63B 37/0003 473/376 |

* cited by examiner

*Primary Examiner* — Raeann Gorden
(74) *Attorney, Agent, or Firm* — Michael A. Catania

(57) ABSTRACT

A golf ball comprising layers that have from 0.05% to 70% by weight of a radio-opaque filler, and wherein the concentration of the radio-opaque filler is measurably different in each layer is disclosed herein. The radio-opaque filler is preferably a compound based on barium, bismuth, tungsten, iodine, or reduced iron.

2 Claims, 9 Drawing Sheets

METHOD AND SYSTEM FOR UTILIZING RADIO-OPAQUE FILLERS IN MULTIPLE LAYERS OF GOLF BALLS

CROSS REFERENCES TO RELATED APPLICATIONS

The Present Application is a continuation-in-part application of U.S. patent application Ser. No. 17/322,584, filed on May 17, 2021, which claims priority to U.S. Provisional Patent Application No. 63/030,494, filed on May 27, 2020, each of which is hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The present invention relates to radio-opaque fillers for a golf ball.

Description of the Related Art

X-ray scanning has been used in the past for golf balls. Marshall et al., U.S. Pat. No. 6,390,937 for a Method For Verifying The Concentricity Of A Multiple-Layer Golf Ball discloses using an X-ray imaging machine to determine the thickness at various locations of a golf ball to ensure concentricity of the golf ball The prior art fails to disclose imaging of multiple layers on a ball through any number of X-ray analysis techniques.

Determination of layer thickness or eccentricity in golf balls via X-ray has been disclosed in prior art. This involves doping a layer with a radio-opaque filler to provide contrast with other layers. However, the prior art refers to only doping a single layer to make measurements. Furthermore, it refers to very specific loadings, materials, and X-ray processes. This art is limiting in that it does not allow for imaging of multiple layers on the ball through any number of X-ray analysis techniques.

BRIEF SUMMARY OF THE INVENTION

The present invention is the doping of multiple golf ball layers with the same or different concentrations of the same or different radio-opaque fillers to provide differential contrast in an X-ray process.

Another aspect of the present invention is a golf ball comprising a center core comprising polybutadiene and a cover layer disposed over the center core. Each of the center core and the cover layer comprises from 0.05% to 70% by weight of radio-opaque filler, and the center core has a concentration of the radio-opaque filler that is measurably different than a concentration of radio-opaque filler in the cover layer.

Yet another aspect of the present invention is a golf ball comprising a center core comprising polybutadiene, an outer core disposed over the center core, an inner mantle layer disposed over the outer core, an outer mantle layer disposed over the inner mantle layer, and a cover layer disposed over the outer mantle layer. Each of the center core outer core, the inner mantle layer, the outer mantle layer and the cover layer comprises from 0.05% to 70% by weight of radio-opaque filler. Each of the center core, outer core, the inner mantle layer, the outer mantle layer and the cover layer has a concentration of the radio-opaque filler that is measurably different than a concentration of radio-opaque filler in any other layer. The inner mantle layer has a thickness ranging from 0.03 inch to 0.09 inch. The inner mantle layer is composed of an ionomer material. The inner mantle layer material has a plaque Shore D hardness ranging from 34 to 55. The outer mantle layer has a thickness ranging from 0.025 inch to 0.050 inch. The cover layer has a thickness ranging from 0.025 inch to 0.040 inch.

Yet another aspect of the present invention is a center core, an outer core, and a cover layer disposed over the outer core. Two of the center core, outer core and the cover layer comprises from 0.05% to 70% by weight of a radio-opaque filler, and wherein the two of the center core, outer core and the cover layer has a concentration of the radio-opaque filler that is measurably different than a concentration of radio-opaque filler in the other layer.

Another aspect of the present invention is a method for utilizing an imaging machine to determine a parameter of a finished golf ball. The method includes loading a golf ball into an imaging machine. The method also includes imaging the golf ball to determine a parameter of the golf ball. The golf ball comprises a center core and a cover layer disposed over the center core. Each of the center core and the cover layer comprises from 0.05% to 70% by weight of a radio-opaque filler. The center core has a concentration of the radio-opaque filler that is measurably different than a concentration of radio-opaque filler in the cover layer.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

The present invention allows for the use of various loadings or filler types in multiple layers on the ball to enable X-ray analysis of those layers, preferably in a single pass. Furthermore, existing prior art may be specific to constructions and materials. This invention may be applied more broadly.

A primary purpose of this invention is to load multiple layers of a golf ball with different concentrations or types of radio-opaque materials, enabling layer thickness and concentricity/eccentricity measurements of multiple layers in a single pass through an X-ray machine. This is performed with any number of X-ray analysis techniques that provide contrast differences between layers. It is possible to measure diameters, thicknesses, and eccentricities of all the layers/components in the ball.

The present invention discloses the loading of multiple layers of a golf ball with various concentrations or types of radio-opaque fillers. Fillers include, but are not limited to, compounds based on barium, bismuth, tungsten, iodine, or reduced iron. The layers comprise the fillers preferably at 0.05% to 70% by weight. Ideally, each layer is doped with different concentrations of the same or different radio-opaque fillers. The X-Ray process is then be able to discern the various layers at either constant or variable X-ray power/intensity.

Features include the doping of multiple golf ball layers with same/different concentrations of same/different radio-opaque fillers to provide differential contrast in and X-ray process.

Figure 1:
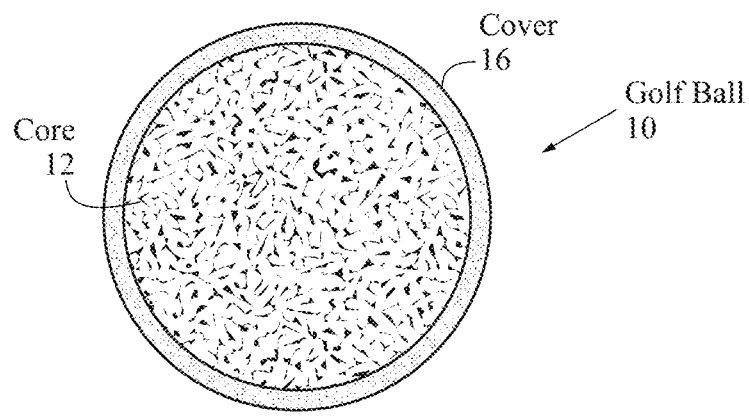
FIG. 1 is a cross-sectional view of a golf ball with a core component and a cover layer, and each layer comprising a radio-opaque filler.

A golf ball 10 comprising a center core 12 made of polybutadiene and a cover 16 layer disposed over the center core 12 is shown in FIG. 1. Each of the center core 12 and the cover layer 16 comprises from 0.05% to 70% by weight of a radio-opaque filler, and the center core 12 has a concentration of the radio-opaque filler that is measurably different than a concentration of radio-opaque filler in the cover 16 layer. The cover layer is preferably composed of an ionomer material.

In a preferred embodiment, the separate layers comprise from 0.05% to 70% by weight of a radio-opaque filler, and the layers each have a concentration of the radio-opaque filler that is measurably different than a concentration of radio-opaque filler in the other layers that contain the radio-opaque filler. The radio-opaque filler is preferably a compound based on barium, bismuth, tungsten, iodine, or reduced iron.

Figure 2:
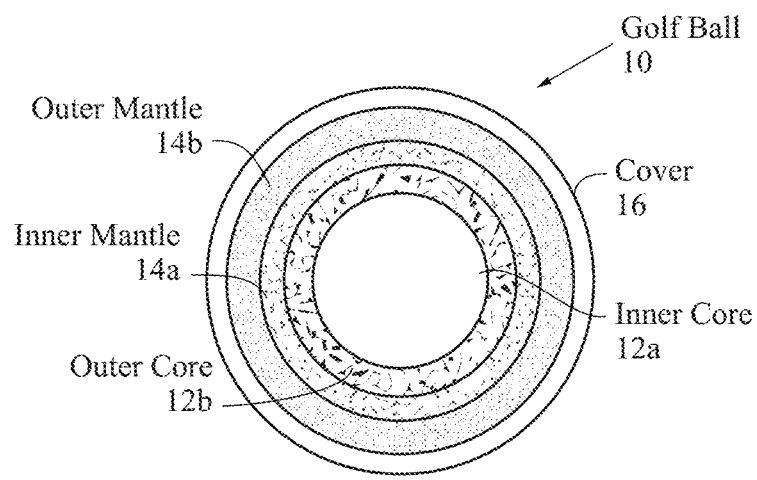
FIG. 2 is a cross-sectional view of a golf ball with an inner core layer, an outer core layer, an inner mantle layer, an outer mantle layer and a cover layer, and some of the layers comprise a radio-opaque filler.

FIG. 2 shows a five layer golf ball 10 further comprising an outer core 12b disposed over the center core 12a, an inner mantle 14a layer disposed over the outer core 12b, an outer mantle 14b layer disposed over the inner mantle 14a layer, and a cover 16 layer disposed over the outer mantle 14b layer.

The inner mantle 14a layer thickness preferably ranges from 0.03 inch to 0.09 inch and is composed of an ionomer material. The inner mantle 14a layer material preferably has a plaque Shore D hardness ranging from 34 to 55. The outer mantle 14b layer thickness preferably ranges from 0.025 inch to 0.050 inch. The cover 16 layer thickness preferably ranges from 0.025 inch to 0.040 inch.

Each of the outer core 12b, the inner mantle 14a layer and the outer mantle 14b layer comprises from 0.05% to 70% by weight of a radio-opaque filler, and each layer has a concentration of the radio-opaque filler that is measurably different than a concentration of radio-opaque filler of any other layer.

In an alternative embodiment, the golf ball 10 comprises of an outer core 12b, a center core 12a, an inner mantle 14a layer, an outer mantle 14b layer, and a cover 16 layer. The inner mantle 14a layer has a thickness ranging from 0.030 inch to 0.090 inch, and a plaque Shore D hardness ranging from 30 to 50. The outer mantle 14b layer has a thickness ranging from 0.025 inch to 0.070 inch, and a plaque Shore D hardness ranging from 50 to 71. The inner mantle 14a is thicker than the outer mantle 14b, and the outer mantle 14b is harder than the inner mantle 14a.

In this alternative embodiment, each of the outer core 12b, the inner mantle layer 14a and the outer mantle 14b layer comprises from 0.05% to 70% by weight of a radio-opaque filler, and each layer has a concentration of the radio-opaque filler that is measurably different than a concentration of radio-opaque filler of any other layer.

In another alternative embodiment, the inner mantle 14a layer has a thickness ranging from 0.070 inch to 0.090 inch, and is composed of an ionomer material. The inner mantle 14a layer material preferably has a plaque Shore D hardness ranging from 36 to 44. In this embodiment, the outer mantle 14b layer has a thickness ranging from 0.025 inch to 0.040 inch, and is composed of an ionomer material. The outer mantle 14b layer material preferably has a plaque Shore D hardness ranging from 65 to 71. Further, in this embodiment, the cover 16 layer having a thickness ranging from 0.025 inch to 0.040 inch.

Figure 3:
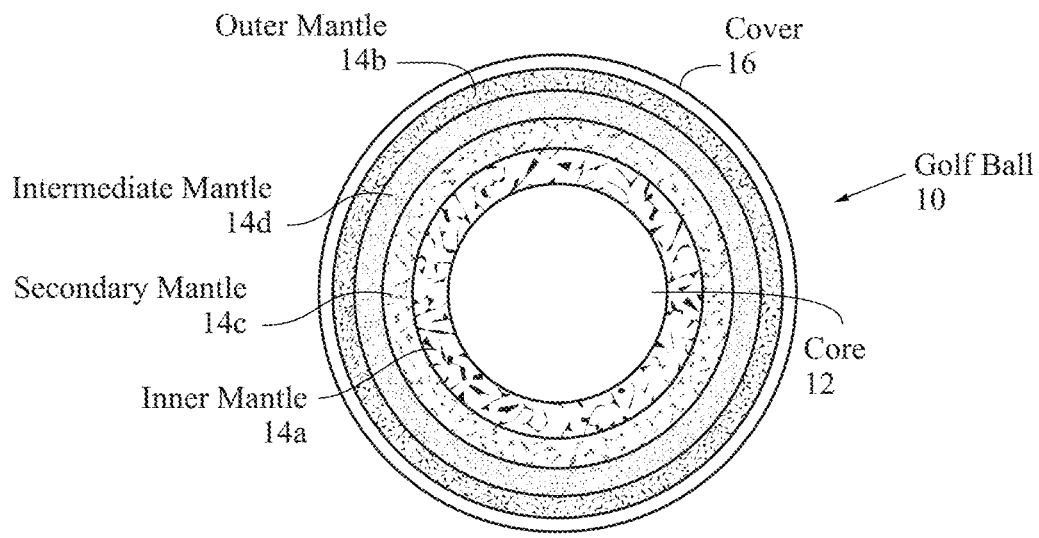
FIG. 3 is a cross-sectional view of a golf ball with a core component, an inner mantle layer, a secondary mantle layer, an intermediate mantle layer, an outer mantle layer and a cover layer, and some of the layers comprise a radio-opaque filler.

FIG. 3 shows an alternative embodiment of a golf ball 10. The golf ball 10 is composed of multiple mantle layers. An inner mantle 14a is disposed over the center core 12, a first center mantle 14c layer over the inner mantle 14a layer, a second center mantle 14d layer over the first center mantle 14c layer, an outer mantle 14b layer over the second center mantle 14d layer, and a cover 16 layer over the outer mantle layer 14b.

In this embodiment, the inner mantle 14a has a thickness ranging from 0.030 inch to 0.050 inch and is composed of an ionomer material. The inner mantle layer material has a plaque Shore D hardness ranging from 30 to 40. The first center mantle 14c layer has a thickness ranging from 0.030 inch to 0.050 inch and is composed of a fully neutralized polymer material. The first center mantle 14c layer material has a plaque Shore D hardness ranging from 40 to 55. The second center mantle 14d layer has a thickness ranging from 0.030 inch to 0.050 inch and is also composed of a fully neutralized polymer material. The second center mantle 14d layer material has a plaque Shore D hardness ranging from 45 to 55. The outer mantle 14b layer has a thickness ranging from 0.030 inch to 0.050 inch and is composed of an ionomer material. The outer mantle 14b layer material has a plaque Shore D hardness ranging from 60 to 75. The cover 16 layer has a thickness ranging from 0.025 inch to 0.040 inch.

Further, in this embodiment, each of the mantle layers 14a-14d comprises from 0.05% to 70% by weight of a radio-opaque filler, and each layer has a concentration of the radio-opaque filler that is measurably different than a concentration of radio-opaque filler of any other layer.

Figure 4:
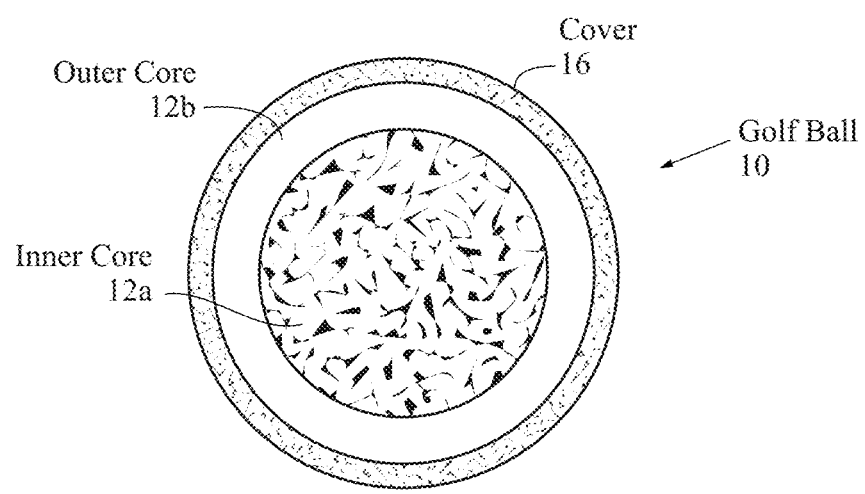
FIG. 4 is a cross-sectional view of a golf ball with an inner core layer, an outer core layer and a cover layer, and some of the layers comprise a radio-opaque filler.

In another alternative embodiment, as shown in FIG. 4, the golf ball 10 comprises of a center core 12a, an outer core 12b, and a cover 16 layer. Preferably, two of the center core 12a, the outer core 12b and the cover 16 layer comprises from 0.05% to 70% by weight of a radio-opaque filler, and the center core 12a has a concentration of the radio-opaque filler that is measurably different than a concentration of radio-opaque filler in the cover 16 layer.

In this embodiment, the radio-opaque filler is preferably a compound based on barium, bismuth, tungsten, iodine, or reduced iron. The cover 16 layer is preferably composed of an ionomer material.

In yet another embodiment, the golf ball comprises of an inner mantle layer, an outer mantle layer, and a cover layer. The inner mantle layer has a thickness ranging from 0.03 inch to 0.09 inch, is composed of an ionomer material, and has a plaque Shore D hardness ranging from 34 to 55. The outer mantle layer has a thickness ranging from 0.025 inch to 0.050 inch. The cover layer has a thickness ranging from 0.025 inch to 0.040 inch.

In this embodiment, at least two of the center core, the outer core, the inner mantle layer, the outer mantle layer and the cover layer comprises from 0.05% to 70% by weight of a radio-opaque filler, and wherein the at least two of the center core, the outer core, the inner mantle layer, the outer mantle layer and the cover layer has a concentration of the radio-opaque filler that is measurably different than a concentration of radio-opaque filler of any other layer.

In yet another embodiment, the golf ball comprises of an inner mantle layer, an outer mantle layer, and a cover layer. The inner mantle layer has a thickness ranging from 0.030 inch to 0.090 inch with a plaque Shore D hardness ranging from 30 to 50. The outer mantle layer has a thickness ranging from 0.025 inch to 0.070 inch with a plaque Shore D hardness ranging from 50 to 71. In this embodiment, the inner mantle is thicker than the outer mantle, and the outer mantle is harder than the inner mantle.

Further, in this embodiment, at least two of the center core, the outer core, the inner mantle layer, the outer mantle layer and the cover layer comprises from 0.05% to 70% by weight of a radio-opaque filler, and wherein the at least two of the center core, the outer core, the inner mantle layer, the outer mantle layer and the cover layer has a concentration of the radio-opaque filler that is measurably different than a concentration of radio-opaque filler of any other layer.

Figure 5:
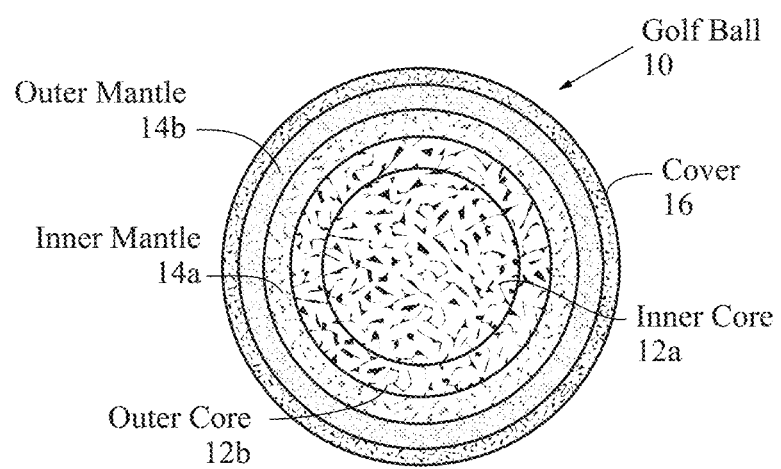
FIG. 5 is a cross-sectional view of a golf ball with an inner core layer, an outer core layer, an inner mantle layer, an outer mantle layer, and a cover layer and each layer comprising a radio-opaque filler.

FIG. 5 shows an alternative embodiment of a golf ball 10. The golf ball 10 is composed of multiple layers. An outer core 12b is disposed over an inner core 12a. An inner mantle 14a is disposed over the outer core 12b, and an outer mantle layer 14b is disposed over the inner mantle layer 14a. A cover layer 16 is disposed over the outer mantle layer 14b. Each of the layers comprises from 0.05% to 70% by weight of radio-opaque filler, and the concentration of the radio-opaque filler is measurably different in each layer.

In one embodiment, the golf ball 10 is a three-piece golf ball with a cover layer 16, a mantle layer 14 and a core 12. The cover layer 16 is preferably composed of a thermoplastic polyurethane material and 0.05% to 70% by weight of radio-opaque filler. In a preferably embodiment, the mantle layer 14 is composed of 30 to 50 weight percent of a first ionomer, 30 to 50 weight percent of a second ionomer, 1 to 20 weight percent of an impact modifier, 5 to 25 weight percent of BaSO4, and 0.1 to 1.0 weight percent of a masterbatch. The core 12 is preferably composed of a first polybutadiene, a second polybutadiene, a zinc diacrylate, a zinc oxide, a zinc stearate, a peroxide, an organic sulfur, and 0.05% to 70% by weight of radio-opaque filler. The core 12 preferably has a density ranging from 1.1 to 1.2, the mantle 14 has a density ranging from 0.9 to 1.0, and the cover 16 preferably has a density ranging from 1.0 to 1.25. The golf ball 10 preferably has a COR of at least 0.75.

In another embodiment, the golf ball 10 has a core 12, an inner mantle layer 14a, an outer mantle layer 14b and a cover layer 16. The core 12 is preferably composed of a first polybutadiene, a second polybutadiene, a zinc diacrylate, a zinc oxide, a zinc stearate, a peroxide, an organic sulfur, and .05% to 70% by weight of radio-opaque filler. The inner mantle 14a is preferably composed of an ionomer blend and 0.5% to 70% by weight of radio-opaque filler. The outer mantle layer 14b is composed of an ionomer blend and 0.5% to 70% by weight of radio-opaque filler. The cover layer 16 is preferably composed of a thermoplastic polyurethane material and 0.5% to 70% by weight of radio-opaque filler. The inner mantle layer 14a preferably has a Shore D hardness ranging from 41-60, the outer mantle layer 14b preferably has a Shore D hardness ranging from 64-71, and the cover layer 16 preferably has a Shore D hardness ranging from 30-40. The core 12 preferably has a diameter ranging from 1.35 to 1.5 inches, the inner mantle layer 14a preferably has a thickness ranging from 0.03 to 0.065 inch, the outer mantle layer 14b preferably has a thickness ranging from 0.03 to 0.070 inch, and the cover layer 16 preferably has a thickness ranging from 0.025 to 0.040 inch.

Figure 6:
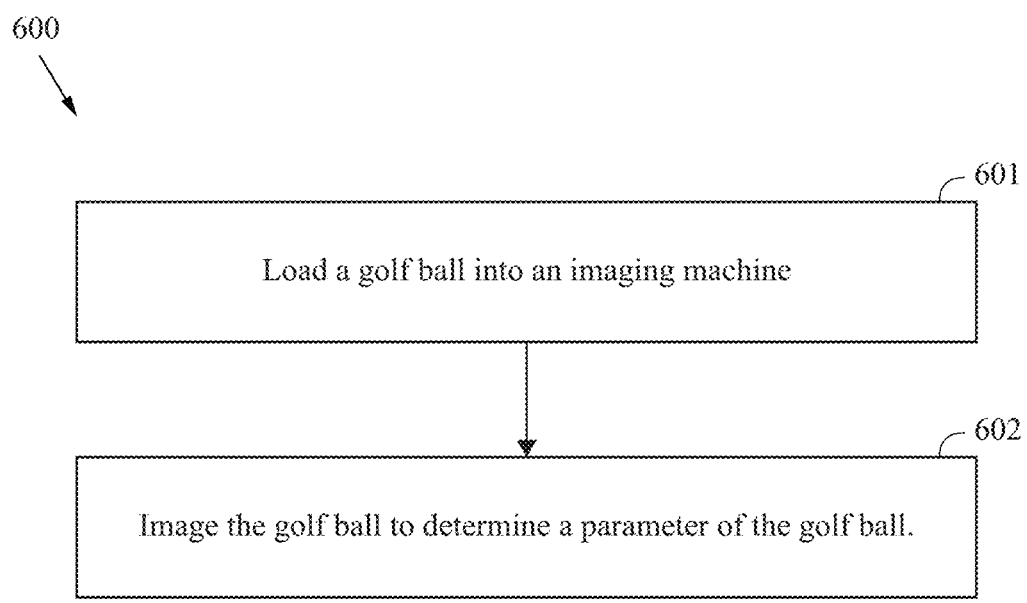
FIG. 6 is a flow chart diagram of a method for utilizing an imaging machine to determine a parameter of a finished golf ball.

FIG. 6 is a flow chart diagram of a method 600 for utilizing an imaging machine to determine a parameter of a finished golf ball following steps 601-602. A golf ball is loaded into an imaging machine, and the golf ball is imaged to determine a parameter of the golf ball. The golf ball preferably comprises a center core and a cover layer, and each layer comprises from 0.05% to 70% by weight of a radio-opaque filler, and each layer has a concentration of the radio-opaque filler that is measurably different than a concentration of radio-opaque filler in the other layer.

The imaging machine is preferably an X-ray machine and the X-Ray process discerns the various layers at either constant or variable X-ray power/intensity.

The parameter is preferably at least one of a diameter, a thickness, or an eccentricity of one or all of the layers of the golf ball.

The golf ball of this method, in an alternative embodiment, comprises an outer core, a center core, an inner mantle layer, an outer mantle layer, and a cover layer. The inner mantle layer has a thickness ranging from 0.03 inch to 0.09 inch, is composed of an ionomer material, and has a plaque Shore D hardness ranging from 34 to 55. The outer mantle layer has a thickness ranging from 0.025 inch to 0.050 inch. The cover layer has a thickness ranging from 0.025 inch to 0.040 inch. Each of the outer core, the inner mantle layer and the outer mantle layer comprises from 0.05% to 70% by weight of a radio-opaque filler, and wherein each of the outer core, the inner mantle layer and the outer mantle layer has a concentration of the radio-opaque filler that is measurably different than a concentration of radio-opaque filler of any other layer.

The golf ball of this method, in yet another alternative embodiment further comprises a mantle layer over the center core wherein the mantle layer further comprises from 0.05% to 70% by weight of a radio-opaque filler.

Figure 7:
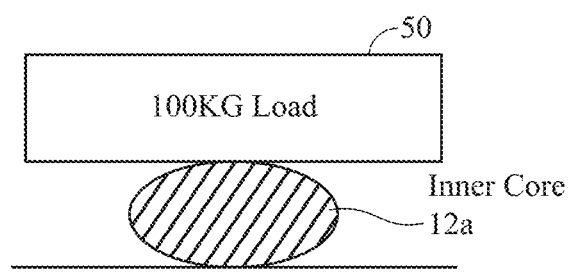
FIG. 7 is a cross-sectional view of an inner core layer under a 100 kilogram load.
Figure 8:
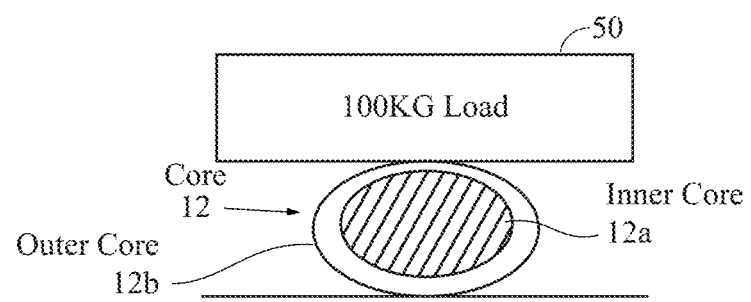
FIG. 8 is a cross-sectional view of a core under a 100 kilogram load.

Preferably the inner core 12a has a deflection of at least 0.230 inch under a load of 220 pounds, and the core 12 has a deflection of at least 0.080 inch under a load of 200 pounds. As shown in FIGS. 7 and 8, a mass 50 is loaded onto an inner core 12a and a core 12. As shown in FIGS. 7 and 8, the mass is 100 kilograms, approximately 220 pounds. Under a load of 100 kilograms, the inner core 12a preferably has a deflection from 0.230 inch to 0.300 inch. Under a load of 100 kilograms, preferably the core 12 has a deflection of 0.08 inch to 0.150 inch. Alternatively, the load is 200 pounds (approximately 90 kilograms), and the deflection of the core 12 is at least 0.080 inch. Further, a compressive deformation from a beginning load of 10 kilograms to an ending load of 130 kilograms for the inner core ranges from 4 millimeters to 7 millimeters and more preferably from 5 millimeters to 6.5 millimeters. The dual core deflection differential allows for low spin off the tee to provide greater distance, and high spin on approach shots.

Figure 9:
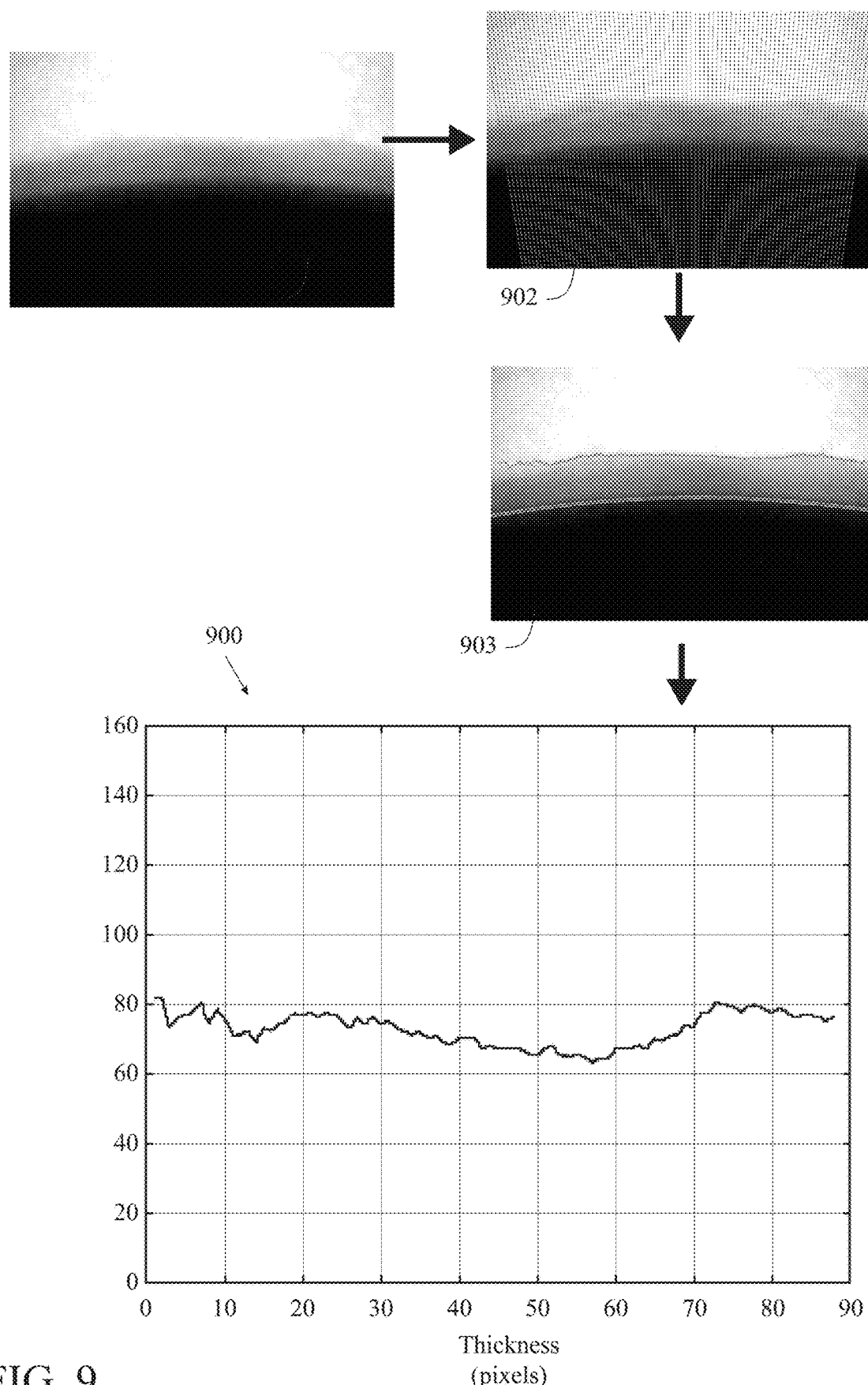
FIG. 9 is a graph of thickness based on pixels.

FIG. 9 shows a process for producing a graph of thickness based on pixels. An initial image 901 is generated. Then at 902 an image with multiple radial rays from a center through the cover is generated. In the image at 903, for each line, edge detection techniques are used to locate the edges of the outer mantle (blue line) and cover (green line). In this case, moving averages were used. With the known edges, the outer edge (cover) is subtracted from the inner edge (outer mantle) to produce a cover thickness in pixels. This is converted to inches or mm with a simple calibration to produce the graph 900.

Figure 10:
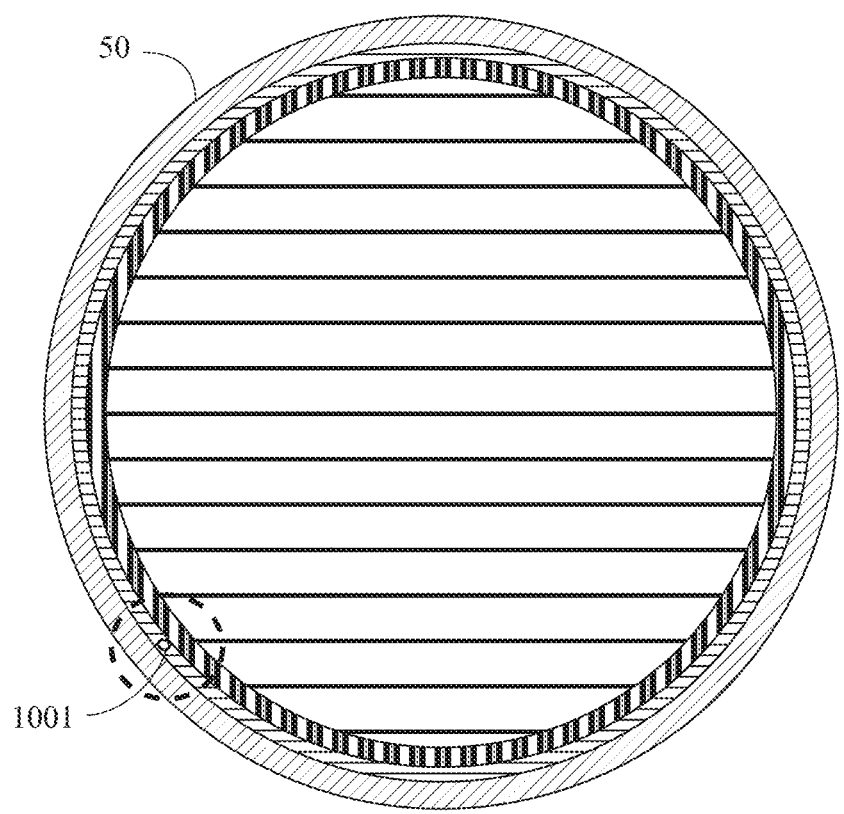
FIG. 10 is an X-ray image of a golf ball.

FIG. 10 is an X-ray image of a golf ball 50. Using the image taken by the X-ray unit, an operator can interrogate a layer for an inclusion 1001. The inclusion 1001 appears as a difference pixelated color indicating it has a significantly different density. When this occurs in the rubber recipe, it is normally darker and indicates that powders are not adequately dispersed within the polymer matrix. An inclusion could lead to a premature durability failure. When an inclusion is found, the software can compare it against a set of criteria and sort the defective sample accordingly.

Figure 11:
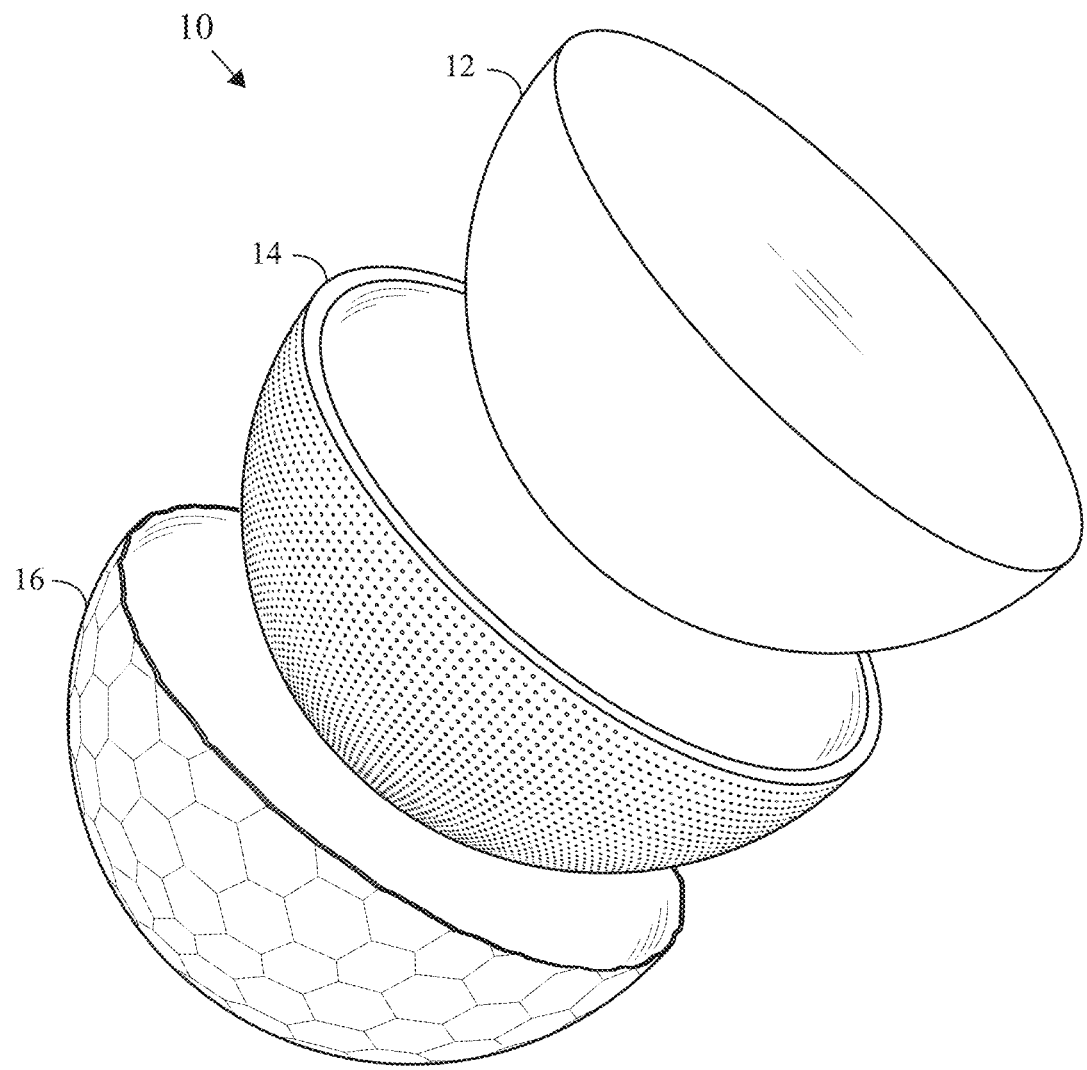
FIG. 11 is a three piece golf ball.

As shown in FIG. 11, a golf ball 10 comprises center core 12, a mantle layer 14 and a cover layer 16. The center core 12 comprises a first polybutadiene, a second polybutadiene, a zinc diacrylate, a zinc oxide, a zinc stearate, a peroxide, an organic sulfur, and 0.05% to 70% by weight of radio-opaque filler. The core 12 preferably has a density ranging from 1.1 to 3.5. The mantle layer 14 is preferably composed of 30 to 50 weight percent of a first ionomer, 30 to 50 weight percent of a second ionomer, 1 to 20 weight percent of an impact modifier, 5 to 25 weight percent of BaSO4, and 0.1 to 1.0 weight percent of a masterbatch. The mantle layer 14 preferably has a density ranging from 0.9 to 1.0. The cover layer 16 is disposed over the mantle layer 14. The cover layer 16 is preferably composed of a thermoplastic polyurethane material and 0.5% to 70% by weight of radio-opaque filler. The cover layer 16 preferably has a density ranging from 1.0 to 3.5. The center core 12 has a concentration of the radio-opaque filler that is measurably different than a concentration of radio-opaque filler in the cover layer 16. The golf ball 10 has a COR of at least 0.75. The radio-opaque filler is a compound preferably based on barium, bismuth, tungsten, iodine, or reduced iron.

Figure 12:
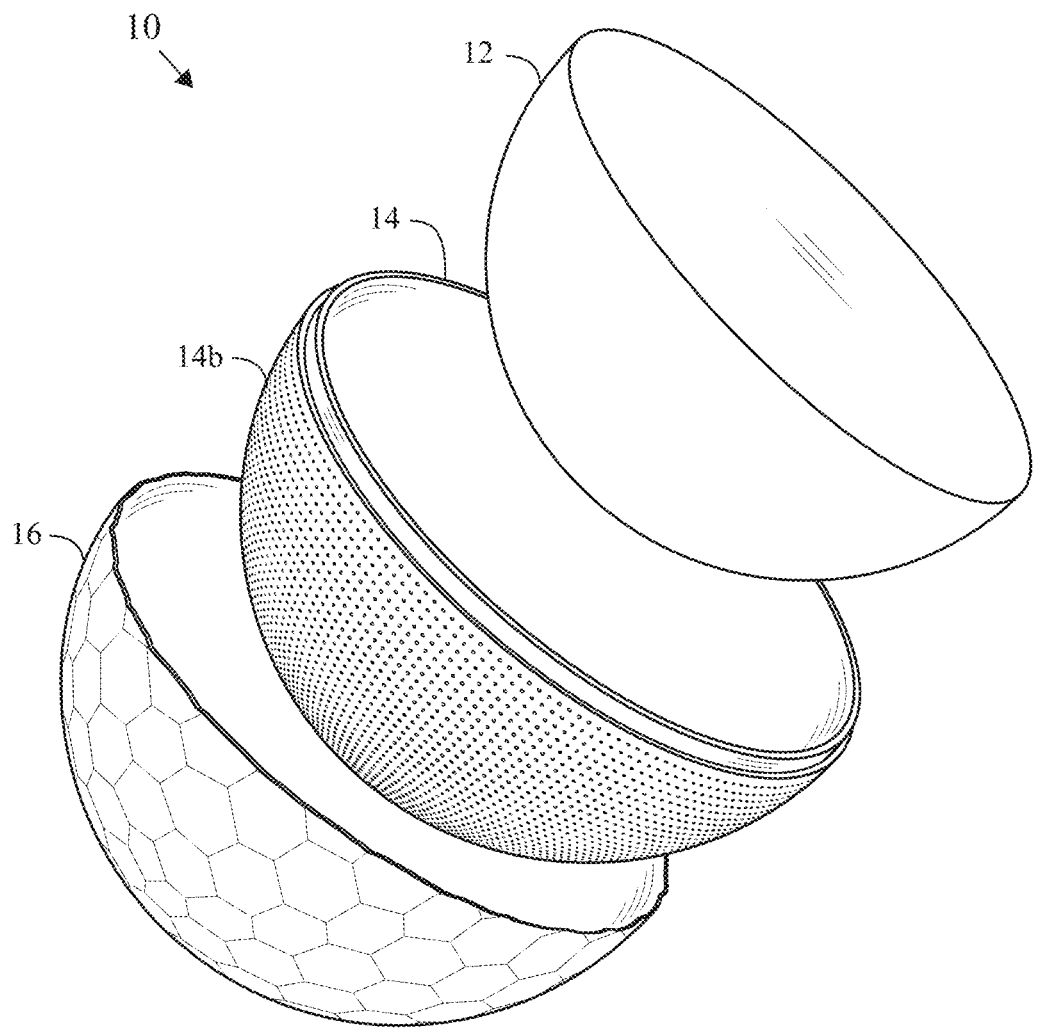
FIG. 12 is a four piece golf ball.

As shown in FIG. 12, a golf ball 10 comprises center core 12, an inner mantle layer 14, an outer mantle layer 14b, and a cover layer 16. The center core 12 comprises a first polybutadiene, a second polybutadiene, a zinc diacrylate, a zinc oxide, a zinc stearate, a peroxide, an organic sulfur, and 0.05% to 70% by weight of radio-opaque filler. The center core 12 has a density ranging from 1.1 to 3.5. The inner mantle layer 14a is preferably composed of an ionomer blend and 0.5% to 70% by weight of radio-opaque filler. The outer mantle layer is preferably composed of an ionomer blend and 0.5% to 70% by weight of radio-opaque filler. The cover layer 16 is disposed over the outer mantle layer 14b. The cover layer 16 is preferably composed of a thermoplastic polyurethane material and 0.5% to 70% by weight of radio-opaque filler. The cover layer preferably has a density ranging from 1.0 to 3.5. The center core 12 has a concentration of the radio-opaque filler that is measurably different than a concentration of radio-opaque filler in the cover layer 16, the inner mantle layer 14a and the outer mantle layer 14b. The golf ball 10 has a COR of at least 0.75. The radio-opaque filler is a compound preferably based on barium, bismuth, tungsten, iodine, or reduced iron.

Preferably, the outer core is composed of a polybutadiene material, zinc penta chloride, organic peroxide, zinc stearate, zinc diacrylate and zinc oxide.

In a preferred embodiment, the cover is preferably composed of a thermoplastic polyurethane material, and preferably has a thickness ranging from 0.025 inch to 0.04 inch, and more preferably ranging from 0.03 inch to 0.04 inch. The material of the cover preferably has a Shore D plaque hardness ranging from 30 to 60, and more preferably from 40 to 50. The Shore D hardness measured on the cover is preferably less than 56 Shore D. Preferably the cover 16 has a Shore A hardness of less than 96. Alternatively, the cover 16 is composed of a thermoplastic polyurethane/polyurea material. One example is disclosed in U.S. Pat. No. 7,367,903 for a Golf Ball, which is hereby incorporated by reference in its entirety. Another example is Melanson, U.S. Pat. No. 7,641,841, which is hereby incorporated by reference in its entirety. Another example is Melanson et al, U.S. Pat. No. 7,842,211, which is hereby incorporated by reference in its entirety. Another example is Matroni et al., U.S. Pat. No. 7,867,111, which is hereby incorporated by reference in its entirety. Another example is Dewanjee et al., U.S. Pat. No. 7,785,522, which is hereby incorporated by reference in its entirety.

The mantle component is preferably composed of the inner mantle layer and the outer mantle layer. The mantle component preferably has a thickness ranging from 0.05 inch to 0.15 inch, and more preferably from 0.06 inch to 0.08 inch. The outer mantle layer is preferably composed of a blend of ionomer materials. One preferred embodiment comprises SURLYN 9150 material, SURLYN 8940 material, a SURLYN AD1022 material, and a masterbatch. The SURLYN 9150 material is preferably present in an amount ranging from 20 to 45 weight percent of the cover, and more preferably 30 to 40 weight percent. The SURLYN 8945 is preferably present in an amount ranging from 15 to 35 weight percent of the cover, more preferably 20 to 30 weight percent, and most preferably 26 weight percent. The SURLYN 9945 is preferably present in an amount ranging from 30 to 50 weight percent of the cover, more preferably 35 to 45 weight percent, and most preferably 41 weight percent. The SURLYN 8940 is preferably present in an amount ranging from 5 to 15 weight percent of the cover, more preferably 7 to 12 weight percent, and most preferably 10 weight percent.

SURLYN 8320, from DuPont, is a very-low modulus ethylene/methacrylic acid copolymer with partial neutralization of the acid groups with sodium ions. SURLYN 8945, also from DuPont, is a high acid ethylene/methacrylic acid copolymer with partial neutralization of the acid groups with sodium ions. SURLYN 9945, also from DuPont, is a high acid ethylene/methacrylic acid copolymer with partial neutralization of the acid groups with zinc ions. SURLYN 8940, also from DuPont, is an ethylene/methacrylic acid copolymer with partial neutralization of the acid groups with sodium ions.

The inner mantle layer is preferably composed of a blend of ionomers, preferably comprising a terpolymer and at least two high acid (greater than 18 weight percent) ionomers neutralized with sodium, zinc, magnesium, or other metal ions. The material for the inner mantle layer preferably has a Shore D plaque hardness ranging preferably from 35 to 77, more preferably from 36 to 44, a most preferably approximately 40. The thickness of the outer mantle layer preferably ranges from 0.025 inch to 0.050 inch, and is more preferably approximately 0.037 inch. The mass of an insert including the dual core and the inner mantle layer preferably ranges from 32 grams to 40 grams, more preferably from 34 to 38 grams, and is most preferably approximately 36 grams. The inner mantle layer is alternatively composed of a HPF material available from DuPont. Alternatively, the inner mantle layer 14b is composed of a material such as disclosed in Kennedy, III et al., U.S. Pat. No. 7,361,101 for a Golf Ball And Thermoplastic Material, which is hereby incorporated by reference in its entirety.

The outer mantle layer is preferably composed of a blend of ionomers, preferably comprising at least two high acid (greater than 18 weight percent) ionomers neutralized with sodium, zinc, or other metal ions. The blend of ionomers also preferably includes a masterbatch. The material of the outer mantle layer preferably has a Shore D plaque hardness ranging preferably from 55 to 75, more preferably from 65 to 71, and most preferably approximately 67. The thickness of the outer mantle layer preferably ranges from 0.025 inch to 0.040 inch, and is more preferably approximately 0.030 inch. The mass of the entire insert including the core, the inner mantle layer and the outer mantle layer preferably ranges from 38 grams to 43 grams, more preferably from 39 to 41 grams, and is most preferably approximately 41 grams.

In an alternative embodiment, the inner mantle layer is preferably composed of a blend of ionomers, preferably comprising at least two high acid (greater than 18 weight percent) ionomers neutralized with sodium, zinc, or other metal ions. The blend of ionomers also preferably includes a masterbatch. In this embodiment, the material of the inner mantle layer has a Shore D plaque hardness ranging preferably from 55 to 75, more preferably from 65 to 71, and most preferably approximately 67. The thickness of the outer mantle layer preferably ranges from 0.025 inch to 0.040 inch, and is more preferably approximately 0.030 inch. Also in this embodiment, the outer mantle layer 14b is composed of a blend of ionomers, preferably comprising a terpolymer and at least two high acid (greater than 18 weight percent) ionomers neutralized with sodium, zinc, magnesium, or other metal ions. In this embodiment, the material for the outer mantle layer 14b preferably has a Shore D plaque hardness ranging preferably from 35 to 77, more preferably from 36 to 44, a most preferably approximately 40. The thickness of the outer mantle layer preferably ranges from 0.025 inch to 0.100 inch, and more preferably ranges from 0.070 inch to 0.090 inch.

In other golf balls, the inner mantle layer is thicker than the outer mantle layer and the outer mantle layer is harder than the inner mantle layer, the inner mantle layer is composed of a blend of ionomers, preferably comprising a terpolymer and at least two high acid (greater than 18 weight percent) ionomers neutralized with sodium, zinc, magnesium, or other metal ions. In this embodiment, the material for the inner mantle layer has a Shore D plaque hardness ranging preferably from 30 to 77, more preferably from 30 to 50, and most preferably approximately 40. In this embodiment, the material for the outer mantle layer has a Shore D plaque hardness ranging preferably from 40 to 77, more preferably from 50 to 71, and most preferably approximately 67. In this embodiment, the thickness of the inner mantle layer preferably ranges from 0.030 inch to 0.090 inch, and the thickness of the outer mantle layer ranges from 0.025 inch to 0.070 inch.

Preferably the inner core has a diameter ranging from 0.75 inch to 1.20 inches, more preferably from 0.85 inch to 1.05 inch, and most preferably approximately 0.95 inch. Preferably the inner core 12a has a Shore D hardness ranging from 20 to 50, more preferably from 25 to 40, and most preferably approximately 35. Preferably the inner core is formed from a polybutadiene, zinc diacrylate, zinc oxide, zinc stearate, a peptizer and peroxide. Preferably the inner core has a mass ranging from 5 grams to 15 grams, 7 grams to 10 grams and most preferably approximately 8 grams.

Preferably the outer core has a diameter ranging from 1.25 inch to 1.55 inches, more preferably from 1.40 inch to 1.5 inch, and most preferably approximately 1.5 inch. Preferably the inner core has a Shore D surface hardness ranging from 40 to 65, more preferably from 50 to 60, and most preferably approximately 56. Preferably the inner core is formed from a polybutadiene, zinc diacrylate, zinc oxide, zinc stearate, a peptizer and peroxide. Preferably the combined inner core and outer core have a mass ranging from 25 grams to 35 grams, 30 grams to 34 grams and most preferably approximately 32 grams.

In a particularly preferred embodiment of the invention, the golf ball preferably has an aerodynamic pattern such as disclosed in Simonds et al., U.S. Pat. No. 7,419,443 for a Low Volume Cover For A Golf Ball, which is hereby incorporated by reference in its entirety. Alternatively, the golf ball has an aerodynamic pattern such as disclosed in Simonds et al., U.S. Pat. No. 7,338,392 for An Aerodynamic Surface Geometry For A Golf Ball, which is hereby incorporated by reference in its entirety.

Various aspects of the present invention golf balls have been described in terms of certain tests or measuring procedures. These are described in greater detail as follows.

As used herein, "Shore D hardness" of the golf ball layers is measured generally in accordance with ASTM D-2240 type D, except the measurements may be made on the curved surface of a component of the golf ball, rather than on a plaque. If measured on the ball, the measurement will indicate that the measurement was made on the ball. In referring to a hardness of a material of a layer of the golf ball, the measurement will be made on a plaque in accordance with ASTM D-2240. Furthermore, the Shore D hardness of the cover is measured while the cover remains over the mantles and cores. When a hardness measurement is made on the golf ball, the Shore D hardness is preferably measured at a land area of the cover.

As used herein, "Shore A hardness" of a cover is measured generally in accordance with ASTM D-2240 type A, except the measurements may be made on the curved surface of a component of the golf ball, rather than on a plaque. If measured on the ball, the measurement will indicate that the measurement was made on the ball. In referring to a hardness of a material of a layer of the golf ball, the measurement will be made on a plaque in accordance with ASTM D-2240. Furthermore, the Shore A hardness of the cover is measured while the cover remains over the mantles and cores. When a hardness measurement is made on the golf ball, Shore A hardness is preferably measured at a land area of the cover The resilience or coefficient of restitution (COR) of a golf ball is the constant "e," which is the ratio of the relative velocity of an elastic sphere after direct impact to that before impact. As a result, the COR ("e") can vary from 0 to 1, with 1 being equivalent to a perfectly or completely elastic collision and 0 being equivalent to a perfectly or completely inelastic collision.

COR, along with additional factors such as club head speed, club head mass, ball weight, ball size and density, spin rate, angle of trajectory and surface configuration as well as environmental conditions (e.g. temperature, moisture, atmospheric pressure, wind, etc.) generally determine the distance a ball will travel when hit. Along this line, the distance a golf ball will travel under controlled environmental conditions is a function of the speed and mass of the club and size, density and resilience (COR) of the ball and other factors. The initial velocity of the club, the mass of the club and the angle of the ball's departure are essentially provided by the golfer upon striking. Since club head speed, club head mass, the angle of trajectory and environmental conditions are not determinants controllable by golf ball producers and the ball size and weight are set by the U.S.G.A., these are not factors of concern among golf ball manufacturers. The factors or determinants of interest with respect to improved distance are generally the COR and the surface configuration of the ball.

The coefficient of restitution is the ratio of the outgoing velocity to the incoming velocity. In the examples of this application, the coefficient of restitution of a golf ball was measured by propelling a ball horizontally at a speed of 125+/−5 feet per second (fps) and corrected to 125 fps against a generally vertical, hard, flat steel plate and measuring the ball's incoming and outgoing velocity electronically. Speeds were measured with a pair of ballistic screens, which provide a timing pulse when an object passes through them. The screens were separated by 36 inches and are located 25.25 inches and 61.25 inches from the rebound wall. The ball speed was measured by timing the pulses from screen 1 to screen 2 on the way into the rebound wall (as the average speed of the ball over 36 inches), and then the exit speed was timed from screen 2 to screen 1 over the same distance. The rebound wall was tilted 2 degrees from a vertical plane to allow the ball to rebound slightly downward in order to miss the edge of the cannon that fired it. The rebound wall is solid steel.

As indicated above, the incoming speed should be 125±5 fps but corrected to 125 fps. The correlation between COR and forward or incoming speed has been studied and a correction has been made over the ±5 fps range so that the COR is reported as if the ball had an incoming speed of exactly 125.0 fps.

The measurements for deflection, compression, hardness, and the like are preferably performed on a finished golf ball as opposed to performing the measurement on each layer during manufacturing.

Preferably, in a five layer golf ball comprising an inner core, an outer core, an inner mantle layer, an outer mantle layer and a cover, the hardness/compression of layers involve an inner core with the greatest deflection (lowest hardness), an outer core (combined with the inner core) with a deflection less than the inner core, an inner mantle layer with a hardness less than the hardness of the combined outer core and inner core, an outer mantle layer with the hardness layer of the golf ball, and a cover with a hardness less than the hardness of the outer mantle layer. These measurements are preferably made on a finished golf ball that has been torn down for the measurements.

Preferably the inner mantle layer is thicker than the outer mantle layer or the cover layer. The dual core and dual mantle golf ball creates an optimized velocity-initial velocity ratio (Vi/IV), and allows for spin manipulation. The dual core provides for increased core compression differential resulting in a high spin for short game shots and a low spin for driver shots. A discussion of the USGA initial velocity test is disclosed in Yagley et al., U.S. Pat. No. 6,595,872 for a Golf Ball With High Coefficient Of Restitution, which is hereby incorporated by reference in its entirety. Another example is Bartels et al., U.S. Pat. No. 6,648,775 for a Golf Ball With High Coefficient Of Restitution, which is hereby incorporated by reference in its entirety.

Marshall et al., U.S. Pat. No. 6,390,937 for a Method For Verifying The Concentricity Of A Multiple Layer Golf Ball is hereby incorporated by reference in its entirety.

Crast et al., U.S. Pat. No. 6,632,877, for a Dual Curable Coating, is hereby incorporated by reference in its entirety.

Skrabski et al., U.S. Pat. No. 6,544,337, for a Golf ball Painting System, is hereby incorporated by reference in its entirety.

Crast et al., U.S. Pat. No. 6,365,679, for a Two component polyurethane clear coat for golf balls, is hereby incorporated by reference in its entirety.

Crast et al., U.S. Pat. No. 6,165,564, for a UV Clearable Clear Coat For Golf Balls, is hereby incorporated by reference in its entirety.

Skrabski et al., U.S. Pat. No. 6,319,563, for a Golf ball Painting Method, is hereby incorporated by reference in its entirety.

Bartels, U.S. Pat. No. 9,278,260, for a Low Compression Three-Piece Golf Ball With An Aerodynamic Drag Rise At High Speeds, is hereby incorporated by reference in its entirety.

Chavan et al, U.S. Pat. No. 9,789,366, for a Graphene Core For A Golf Ball, is hereby incorporated by reference in its entirety.

Chavan et al, U.S. patent application Ser. No. 15/705,011, filed on Sep. 14, 2017, for a Graphene Core For A Golf Ball, is hereby incorporated by reference in its entirety.

Chavan et al, U.S. patent application Ser. No. 15/729,231, filed on Oct. 10, 2017, for a Graphene And Nanotube Reinforced Golf Ball, is hereby incorporated by reference in its entirety.

Petrich et al, U.S. Pat. No. 10,695,616 for a Graphene Core For A Golf Ball With A Soft Cover, is hereby incorporated by reference in its entirety.

Jeon, U.S. Pat. No. 10,709,937 for a Golf Ball Core, is hereby incorporated by reference in its entirety.

Caterina et al., U.S. Pat. No. 11,058,924, for a Method And System Utilizing Imaging Analysis For Golf Balls is hereby incorporated by reference in its entirety.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes, modifications and substitutions of equivalents may be made therein without departing from the spirit and scope of this invention which is intended to be unlimited by the foregoing except as may appear in the following appended claims. Therefore, the embodiments of the invention in which an exclusive property or privilege is claimed are defined in the following appended claims.

I claim as my invention the following:

1. A golf ball comprising:

a center core comprising a first polybutadiene, a second polybutadiene, a zinc diacrylate, a zinc oxide, a zinc stearate, a peroxide, an organic sulfur, and 0.05% to 70% by weight of radio-opaque filler, wherein the core has a density ranging from 1.1 to 3.5;

an inner mantle layer composed of an ionomer blend and 0.5% to 70% by weight of radio-opaque filler;

an outer mantle layer composed of an ionomer blend and 0.5% to 70% by weight of radio-opaque filler; and a cover layer disposed over the outer mantle layer, the cover layer is preferably composed of a thermoplastic polyurethane material and 0.5% to 70% by weight of radio-opaque filler, wherein the cover layer has a density ranging from 1.0 to 3.5;

wherein the center core has a concentration of the radio-opaque filler that is measurably different than a concentration of radio-opaque filler in the cover layer;

wherein the radio-opaque filler is an iodine-based compound;

wherein the golf ball has a COR of at least 0.75.

2. A golf ball comprising:

a center core comprising a first polybutadiene, a second polybutadiene, a zinc diacrylate, a zinc oxide, a zinc stearate, a peroxide, an organic sulfur, and 0.05% to 70% by weight of radio-opaque filler, wherein the core has a density ranging from 1.1 to 3.5;

a mantle layer composed of 30 to 50 weight percent of a first ionomer, 30 to 50 weight percent of a second ionomer, 1 to 20 weight percent of an impact modifier, 5 to 25 weight percent of $BaSO_4$, and 0.1 to 1.0 weight percent of a masterbatch, wherein the mantle layer has a density ranging from 0.9 to 1.0; and a cover layer disposed over the mantle layer, the cover layer is preferably composed of a thermoplastic polyurethane material and 0.5% to 70% by weight of radio-opaque filler, wherein the cover layer has a density ranging from 1.0 to 3.5;

wherein the center core has a concentration of the radio-opaque filler that is measurably different than a concentration of radio-opaque filler in the cover layer;

wherein the radio-opaque filler is an iodine-based compound;

wherein the golf ball has a COR of at least 0.75.

* * * * *